(12) United States Patent
Huber et al.

(10) Patent No.: US 10,436,692 B2
(45) Date of Patent: Oct. 8, 2019

(54) MEASURING ARRANGEMENT AND METHOD FOR MEASURING THE DENSITY OF FLOWABLE MEDIA

(71) Applicant: Endress + Hauser Flowtec AG, Reinach (CH)

(72) Inventors: Christof Huber, Bern (CH); Ton Leenhoven, Flayosc (FR)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 95 days.

(21) Appl. No.: 15/535,459

(22) PCT Filed: Nov. 18, 2015

(86) PCT No.: PCT/EP2015/076903
§ 371 (c)(1),
(2) Date: Jun. 13, 2017

(87) PCT Pub. No.: WO2016/096297
PCT Pub. Date: Jun. 23, 2016

(65) Prior Publication Data
US 2017/0343457 A1    Nov. 30, 2017

(30) Foreign Application Priority Data
Dec. 19, 2014    (DE) .................. 10 2014 119 212

(51) Int. Cl.
*G01N 9/00*     (2006.01)
*G01N 11/04*    (2006.01)
(Continued)

(52) U.S. Cl.
CPC ............... *G01N 9/002* (2013.01); *G01N 9/32* (2013.01); *G01N 11/04* (2013.01); *G01N 11/08* (2013.01); *G01N 2009/006* (2013.01)

(58) Field of Classification Search
CPC .......... G01N 9/002; G01N 9/32; G01N 11/04; G01N 11/08; G01N 2009/006
See application file for complete search history.

(56) References Cited

U.S. PATENT DOCUMENTS 3,934,127 A * 1/1976 Schlatter ............... G01F 15/046
                                                        702/46
5,295,084 A * 3/1994 Arunachalam ....... G01F 1/8413
                                                        702/50
(Continued)

FOREIGN PATENT DOCUMENTS

CN          1195401 A       10/1998
CN        101076710 A       11/2007
(Continued)

OTHER PUBLICATIONS

Kalotay, P., "Density and Viscosity Monitoring Systems using Coriolis Flow Meters", ISA Transactions, Instrument Society of America, Pittsburg, PA., Nov. 1999.
(Continued)

*Primary Examiner* — David J Bolduc
(74) *Attorney, Agent, or Firm* — Bacon & Thomas, PLLC

(57) ABSTRACT

An arrangement for measuring density of flowable media includes: a fluid path for conveying a medium; a pump for driving a defined volume flow of the medium in the fluid path; a pressure difference measuring arrangement for registering a pressure drop due to the volume flow of the medium between first and second pressure taps in the fluid path; a densimeter having at least one oscillator, which has at least one oscillatable measuring tube for conveying the medium, at least one exciter mechanism for exciting oscillations of the measuring tube, and at least one sensor arrangement for registering at least one oscillatory characteristic of the oscillator. The at least one measuring tube is arranged in the fluid path. An evaluation apparatus ascer-
(Continued)

tains the density of the medium based on the volume flow, the volume flow dependent pressure drop and the at least one oscillatory characteristic of the oscillator.

24 Claims, 1 Drawing Sheet

(51) Int. Cl.
*G01N 9/32* (2006.01)
*G01N 11/08* (2006.01)

(56) References Cited

U.S. PATENT DOCUMENTS

| | | | |
|---|---|---|---|
| 5,359,881 A | 11/1994 | Kalotay | |
| 5,597,949 A | 1/1997 | Kalotay | |
| 5,661,232 A * | 8/1997 | Van Cleve | G01F 1/8459 |
| | | | 73/32 R |
| 5,687,100 A * | 11/1997 | Buttler | G01F 1/8413 |
| | | | 702/100 |
| 6,196,058 B1 | 3/2001 | Chen | |
| 6,311,136 B1 * | 10/2001 | Henry | G01F 1/8404 |
| | | | 702/45 |
| 7,072,775 B2 * | 7/2006 | Hemp | G01F 1/74 |
| | | | 702/33 |
| 7,716,995 B2 * | 5/2010 | Patten | G01F 1/8413 |
| | | | 73/861.355 |
| 7,823,445 B2 | 11/2010 | Sparks | |
| 2006/0169038 A1 * | 8/2006 | Sparks | G01F 1/8413 |
| | | | 73/202 |
| 2009/0090504 A1 * | 4/2009 | Weightman | E21B 43/26 |
| | | | 166/250.01 |
| 2009/0145198 A1 * | 6/2009 | Sparks | G01F 1/8445 |
| | | | 73/31.03 |
| 2009/0235735 A1 * | 9/2009 | Tsypko | G01F 1/6847 |
| | | | 73/204.24 |
| 2014/0053637 A1 * | 2/2014 | Quillien | G01N 1/2035 |
| | | | 73/54.01 |
| 2016/0281708 A1 * | 9/2016 | Kammerstetter | G01F 15/02 |
| 2017/0343457 A1 | 11/2017 | Huber | |

FOREIGN PATENT DOCUMENTS

| | | |
|---|---|---|
| CN | 101889204 A | 11/2010 |
| DE | 69605429 T2 | 5/2000 |
| DE | 102014119212 A1 | 6/2016 |
| WO | 9709601 A1 | 3/1997 |
| WO | 2009076287 A2 | 6/2009 |

OTHER PUBLICATIONS

German Search Report, German Patent Office, Munich, DE, dated Jul. 23, 2015.
International Search Report, EPO, The Netherlands, dated Feb. 26, 2016.
English Translation of the International Preliminary Report on Patentability, WIPO, Geneva, CH, dated Jun. 29, 2017.
Chinese Office Action in corresponding Chinese Application No. 201580069656.1, dated Feb. 2, 2019.

* cited by examiner

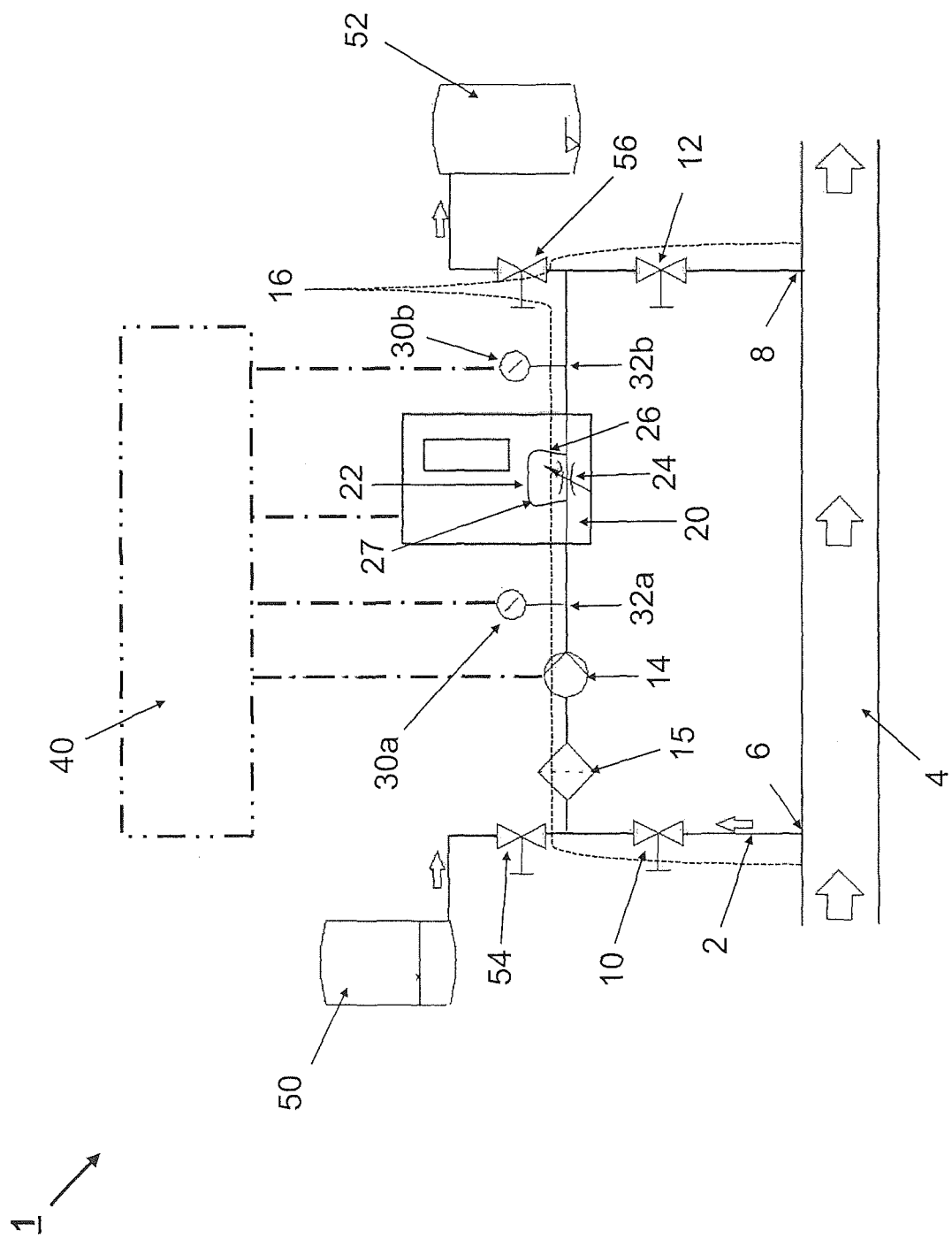

MEASURING ARRANGEMENT AND METHOD FOR MEASURING THE DENSITY OF FLOWABLE MEDIA

TECHNICAL FIELD

The present invention relates to a measuring arrangement and method for measuring the density of flowable media, especially with an oscillating measuring tube, which contains the measured material.

BACKGROUND DISCUSSION

Based on the oscillatory characteristics, especially the resonant frequency of the measuring tube, the density can be determined. Such measuring apparatuses have a cross-sensitivity to the viscosity of the medium. This increases with decreasing measuring tube diameter. On the other hand, straight measuring tubes with small diameters enable a density measurement with very small sample amounts. Additionally, measuring tubes with small diameters tend to have a higher eigenfrequency, so that an exact frequency measurement is easy to implement. Insofar, density measurements with oscillating measuring tubes are quite attractive, wherein, especially in the case of measuring tubes with small diameters, the cross-sensitivity to viscosity must be taken into consideration.

Kalotay et al. describe in U.S. Pat. No. 5,359,881 a viscosimeter, which has a Coriolis mass flow measuring device with integrated pressure difference sensor, which ascertains the pressure drop across the measuring tubes of the Coriolis mass flow measuring device. Based on the mass flow ascertained by means of the Coriolis mass flow measuring device and the density ascertained by means of the Coriolis mass flow measuring device, the volume flow is ascertained, based on which, taking into consideration also the pressure drop, the viscosity is determined. The volume flow, which is taken into consideration for viscosity determination, is based, however, exactly on the defective density measurement.

SUMMARY OF THE INVENTION

It is, consequently, an object of the invention to remedy this situation.

The object is achieved according to the invention by a measuring arrangement and a method for determining the density of a medium.

The measuring arrangement of the invention for measuring the density of flowable media, comprises:

A fluid path for conveying a medium;

a pump, which is arranged in the fluid path, for driving a defined volume flow of the medium in the fluid path;

a pressure difference measuring arrangement for registering a pressure drop due to the volume flow of the medium between a first pressure tap in the fluid path and a second pressure tap in the fluid path; and a densimeter comprising at least one oscillator, which has at least one oscillatable measuring tube for conveying the medium, at least one exciter mechanism for exciting oscillations of the measuring tube, and at least one sensor arrangement for registering at least one oscillatory characteristic of the oscillator, wherein the measuring tube or the measuring tubes of the at least one oscillator is/are arranged in the fluid path;

an evaluation apparatus, which is adapted to ascertain the density of the medium based on the volume flow, the volume flow dependent pressure drop and the at least one oscillatory characteristic of the oscillator.

In a further development of the invention, the evaluation apparatus is adapted, first, to ascertain the viscosity of the medium based on the volume flow and the volume flow dependent pressure drop, and then to ascertain the density of the medium based on this ascertained viscosity and the at least one oscillatory characteristic of the oscillator.

In a further development of the invention, the at least one oscillatory characteristic of the oscillator comprises a resonant frequency of the oscillator dependent on the density of the medium and its viscosity.

In a further development of the invention, the pump comprises a dosing or metering pump, especially a micro annular gear pump with an accuracy of better than 1%.

In a further development of the invention, the at least one measuring tube of the at least one oscillator is arranged, with reference to the volume flow of the medium, between the first pressure tap and the second pressure tap.

In a further development of the invention, the at least one measuring tube of the at least one oscillator has an inner diameter of no more than 1 mm, especially no more than 500 µm, preferably no more than 300 µm, and further preferably no more than 200 µm, for example 160 µm.

In a further development of the invention, the at least one oscillator has a fundamental mode of a bending oscillation with a resonant frequency of not less than 1 kHz, especially not less than 5 kHz and preferably not less than 10 kHz as well as no more than 500 kHz, especially no more than 100 kHz and preferably no more than 50 kHz, when the at least one measuring tube of the oscillator is filled with water.

Suitable densimeters are disclosed, for example, in the international publication WO 2009/076287 A2.

BRIEF DESCRIPTION OF THE DRAWING

The invention will now be explained in greater detail based on an example of an embodiment illustrated in the drawing, the sole figure of which shows as follows:

FIG. 1 is a schematic representation of an example of an embodiment of a measuring arrangement of the invention.

In a further development of the invention, the pressure difference measuring arrangement includes a first pressure sensor, which registers a pressure at the first pressure tap point, and a second pressure sensor, which registers a pressure at the second pressure tap point, wherein the first pressure sensor and the second pressure sensor are absolute pressure sensors or relative pressure sensors.

In a further development of the invention, the densimeter includes a MEMS sensor, which includes the at least one measuring tube of the at least one oscillator.

In a further development of the invention, the MEMS sensor further includes a temperature sensor for providing a measured value of temperature dependent on the media temperature.

In a further development of the invention, the fluid path includes a bypass line with an inner diameter, which is not less than fivefold, especially not less than tenfold and preferably not less than 20 fold the diameter of the measuring tube of the oscillator.

In a further development of the invention, the pump is arranged in the bypass line.

In a further development of the invention, the bypass line includes a throttle, wherein the at least one measuring tube of the at least one oscillator is connected in parallel with the throttle via two branches in the bypass line, between which the throttle is arranged.

In a further development of the invention, the two branches are arranged between the two pressure tap points.

The method of the invention for determining the density of a medium, especially by means of a measuring arrangement of the invention, includes steps as follows:

driving a defined volume flow of the medium in a fluid path;

registering a pressure drop due to the volume flow of the medium between a first pressure tap in the fluid path and a second pressure tap in the fluid path;

registering at least one oscillatory characteristic of an oscillator, which has at least one oscillatable measuring tube for conveying the medium in the fluid path; and ascertaining the density based on the volume flow, the volume flow dependent pressure drop and the at least one oscillatory characteristic of the oscillator.

In a further development of the invention, first, based on the volume flow and the volume flow dependent pressure drop, the viscosity of the medium is ascertained, wherein then, based on this ascertained viscosity and the at least one oscillatory characteristic of the oscillator, the density of the medium is ascertained.

In a further development of the invention, the at least one oscillatory characteristic of the oscillator is a resonant frequency of the oscillator dependent on the density of the medium and its viscosity.

The measuring arrangement of the invention and the method of the invention are suitable for media with a viscosity of greater than 50 mPas, for example, up to 500 mPas, especially up to 1000 mPas. Such viscosities occur, for example, in the case of crude petroleum.

Insofar as the density determination of the invention is at a known temperature, calculation back to a reference density at 15° C. can occur according to API 11.1.

The invention will now be explained in greater detail based on an example of an embodiment illustrated in the drawing, the sole FIGURE of which shows as follows:

FIG. 1 a schematic representation of an example of an embodiment of a measuring arrangement of the invention:

DETAILED DISCUSSION IN CONJUNCTION WITH THE DRAWINGS

The measuring arrangement 1 includes a sampling line 2, which extends in parallel with a pipeline 4 between a first connection point 6 and a second connection point 8, wherein the sampling line is isolateable here via a first valve 10 near the first connection point 6 and a second valve 12 near the second connection point 8. The measuring arrangement 1 includes in the sampling line 2, furthermore, a micro annular gear pump 14, such as one obtainable from the firm HNP, or another dosing or metering pump, with a supply accuracy of better than 1%, especially better than 0.5%, for driving a defined volume flow through the fluid path 16 formed by the sampling line 2 and the therein arranged components. The sampling line has, for example, an inner diameter of 4 mm. Arranged in the sampling line 2 before the annular gear pump 14 is a filter element 15, which has, for example, a maximum pore size of no more than 20 µm, especially no more than 10 µm and preferably no more than 5 µm, in order to assure that subsequent components do not get plugged.

Also arranged in the sampling line 2 is a densimeter 20 having an oscillatable measuring tube 22, which is excitable by means of an exciter to execute bending oscillations, whose resonant frequency depends on the density of a medium contained in the measuring tube. The resonant frequency has a cross sensitivity to the viscosity of the medium, so that viscosity must likewise be ascertained. The measuring tube has a diameter of, for example, 160 µm and is prepared by means of MEMS technology in silicon. The resonant frequency in the case of a density of $10^6$ g/m$^3$ and a low viscosity medium lies, for example, in the order of magnitude of 20 kHz.

The total length of a liquid path section through the measuring tube 22 and surrounding MEMS components with an inner diameter of 200 µm amounts to, for instance, 1 cm. This liquid path section has a comparatively large flow resistance, so that it is not practical to lead the entire volume flow of the sampling line 2 through this liquid path section. The expected volume flows in the case of pressure drops of some bar across the liquid path section through the measuring tube would be small such that the medium in the sampling line 2, especially in the case of changing properties of the medium in the pipeline 4, would not be reliably representative. Therefore, the liquid path section through the MEMS components is led as a bypass 26 parallel to a diaphragm 24, wherein the bypass 26 has a bypass path length of less than 20 mm, especially less than 15 mm, for example, 10 mm. The diaphragm 24 has a diameter of 0.5 to 2 mm, which is so selected that, due to the volume flow in the sampling line 2, a pressure gradient is produced, which drives a fraction of the volume flow of, for example, 0.1% to 5% through the bypass 26. The MEMS components further comprise a temperature sensor 27, for example, a semiconductor resistance element, or a Pt resistance element, which especially registers a temperature of the measuring tube 22 or of the vicinity of the measuring tube, which is representative for the temperature of the medium.

The measuring arrangement 1 further includes a pressure difference measuring arrangement 30 for ascertaining a pressure difference between a first pressure tap point 32a and a second pressure tap point 32b on the sampling line 2, wherein the bypass 26 is connected to the sampling line between the two pressure tap points 32a, 32b. The pressure difference measuring arrangement includes in this embodiment a first relative pressure measuring transducer 30a, which registers a first pressure at the first pressure tap 32a, and a second relative pressure measuring transducer 30b, which registers a second pressure at the second pressure tap 32b.

The measuring arrangement 1 further includes an evaluation unit 40, which is adapted to determine a current viscosity measured value based on the values for volume flow and the associated pressure difference and to calculate, based on the measured resonant frequency, or an uncorrected density measured value derived therefrom, a density measured value corrected relative to the influence of the viscosity. Furthermore, due to the known temperature at the density determination, this can be converted to a reference density at 15° C. according to API 11.1.

The electrical circuits of the pressure difference measuring arrangement, the densimeter 20, as well as the evaluation unit are preferably embodied to meet ignition protection type Ex-i (intrinsically safe). The electronic circuit of the annular gear pump 14 is preferably likewise implemented to meet an ignition protection type, for example with pressure resistant encapsulation according to class Ex-d.

The measuring arrangement can further include an auxiliary medium reservoir 50 and a collecting container 52 connected to the sampling line 2 via branch lines located, respectively, between the first valve 10 and the filter 15, and between the second relative pressure measuring transducer 30b and the second valve 12. The branch lines are isolateable from the sampling line via a third valve 54, and a fourth valve 56, respectively. The auxiliary medium can be, on the one hand, a cleaning liquid, for example, gasoline, or a reference medium having a defined viscosity for calibrating the measuring apparatus.

The invention claimed is:

1. A measuring arrangement for measuring the density of flowable media, comprising:
   a fluid path for conveying a medium;
   a pump, which is arranged in the fluid path, for driving a defined volume flow of the medium in the fluid path, said pump comprising a dosing or metering pump with an accuracy of better than 1%;
   a pressure difference measuring arrangement for registering a pressure drop due to the volume flow of the medium between a first pressure tap and a second pressure tap in the fluid path;
   a densimeter comprising at least one oscillator, which has at least one oscillatable measuring tube for conveying the medium, at least one exciter mechanism for exciting oscillations of the measuring tube, and at least one sensor arrangement for registering a resonant frequency of the oscillator, wherein the measuring tube or the measuring tubes of the at least one oscillator is/are arranged in the fluid path; and
   an evaluation apparatus, which is adapted to ascertain the density of the medium based on the volume flow, the volume flow dependent pressure drop and the resonant frequency of the oscillator.

2. The measuring arrangement as claimed in claim 1, wherein:
   said evaluation apparatus is adapted, first, to ascertain the viscosity of the medium based on the volume flow and the volume flow dependent pressure drop, and then to ascertain the density of the medium based on this ascertained viscosity and the resonant frequency of the oscillator.

3. The measuring arrangement as claimed in claim 1, wherein:
   said pump comprises a micro annular gear pump.

4. The measuring arrangement as claimed in claim 1, wherein:
   said at least one measuring tube of said at least one oscillator is arranged, with reference to the volume flow of the medium, between said first pressure tap and said second pressure tap.

5. The measuring arrangement as claimed in claim 1, wherein:
   said at least one measuring tube of the at least one oscillator has an inner diameter of no more than 1 mm.

6. The measuring arrangement as claimed in claim 1, wherein:
   said at least one oscillator has a fundamental mode of a bending oscillation with a resonant frequency of not less than 1 kHz, when said at least one measuring tube of the oscillator is filled with water.

7. The measuring arrangement as claimed in claim 1, wherein:
   said pressure difference measuring arrangement has a first pressure sensor, which registers a pressure at said first pressure tap point, and a second pressure sensor, which registers a pressure at said second pressure tap point, wherein the first pressure sensor and the second pressure sensor are absolute pressure sensors or relative pressure sensors.

8. The measuring arrangement as claimed in claim 1, wherein:
   said densimeter includes a MEMS sensor, which includes the at least one measuring tube of the at least one oscillator.

9. The measuring arrangement as claimed in claim 8, wherein:
   said MEMS sensor further includes a temperature sensor for providing a measured value of temperature dependent on the media temperature.

10. The measuring arrangement as claimed in claim 1, wherein:
    the fluid path includes a bypass line with an inner diameter, which is not less than fivefold, especially not less than tenfold and preferably not less than 20 fold the diameter of the measuring tube of the oscillator.

11. The measuring arrangement as claimed in claim 10, wherein:
    said pump is arranged in said bypass line.

12. The measuring arrangement as claimed in claim 11, wherein:
    said bypass line has a throttle, wherein said at least one measuring tube of said at least one oscillator is connected in parallel with the throttle via two branches in the bypass line, between which the throttle is arranged.

13. The measuring arrangement as claimed in claim 12, wherein:
    the two branches are arranged between said two pressure tap points.

14. A method for determining the density of a medium, wherein the method comprises steps as follows:
    driving a defined volume flow of the medium in a fluid path with an accuracy of better than 1%;
    registering a pressure drop due to the volume flow of the medium between a first pressure tap in the fluid path and a second pressure tap in the fluid path;
    registering a resonant frequency of an oscillator, which has at least one oscillatable measuring tube for conveying the medium in the fluid path; and
    ascertaining the density based on the volume flow, the volume flow dependent pressure drop and the resonant frequency of the oscillator.

15. The method as claimed in claim 14, wherein:
    first, based on the volume flow and the volume flow dependent pressure drop, the viscosity of the medium is ascertained and then, based on this ascertained viscosity and the resonant frequency of the oscillator, the density of the medium is ascertained.

16. The measuring arrangement as claimed in claim 1, wherein:
    said at least one measuring tube of the at least one oscillator has an inner diameter of no more than 500 μm.

17. The measuring arrangement as claimed in claim 1, wherein:
    said at least one measuring tube of the at least one oscillator has an inner diameter of no more than 300 μm.

18. The measuring arrangement as claimed in claim 1, wherein:
    said at least one measuring tube of the at least one oscillator has an inner diameter of no more than 200 pm.

19. The measuring arrangement as claimed in claim 1, wherein:
    said at least one measuring tube of the at least one oscillator has an inner diameter of about 160 pm.

20. The measuring arrangement as claimed in claim 1, wherein:

said at least one oscillator has a fundamental mode of a bending oscillation with a resonant frequency of not less than 5 kHz, when said at least one measuring tube of the oscillator is filled with water.

21. The measuring arrangement as claimed in claim 1, wherein:

said at least one oscillator has a fundamental mode of a bending oscillation with a resonant frequency of not less than 10 kHz, when said at least one measuring tube of the oscillator is filled with water.

22. The measuring arrangement as claimed in claim 1, wherein:

said at least one oscillator has a fundamental mode of a bending oscillation with a resonant frequency of not more than 500 kHz, when said at least one measuring tube of the oscillator is filled with water.

23. The measuring arrangement as claimed in claim 1, wherein:

said at least one oscillator has a fundamental mode of a bending oscillation with a resonant frequency of not more than 100 kHz, when said at least one measuring tube of the oscillator is filled with water.

24. The measuring arrangement as claimed in claim 1, wherein:

said at least one oscillator has a fundamental mode of a bending oscillation with a resonant frequency of not more than 50 kHz, when said at least one measuring tube of the oscillator is filled with water.

* * * * *